US007618159B2

(12) United States Patent
Tamburrino et al.

(10) Patent No.: US 7,618,159 B2
(45) Date of Patent: Nov. 17, 2009

(54) VENTED IRIS CONTROL FOR LUMINAIRE

(75) Inventors: Richard A. Tamburrino, Auburn, NY (US); Roger W. Leseberg, Syracuse, NY (US); Michael T. McMahon, Syracuse, NY (US); Ervin Goldfain, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 11/691,958

(22) Filed: Mar. 27, 2007

(65) Prior Publication Data

US 2008/0239727 A1 Oct. 2, 2008

(51) Int. Cl.

| | |
|---|---|
| ***F21V 17/02*** | (2006.01) |
| ***A61B 1/06*** | (2006.01) |
| ***G02B 6/08*** | (2006.01) |
| ***F21V 21/08*** | (2006.01) |
| ***G02B 6/06*** | (2006.01) |

(52) U.S. Cl. ....................... 362/321; 362/572; 362/580; 362/103; 362/804; 385/118

(58) Field of Classification Search ......... 362/572–575, 362/580, 103, 105, 321, 804; 385/118
See application file for complete search history.

(56) References Cited

U.S. PATENT DOCUMENTS 4,104,709 A 8/1978 Kloots
4,234,910 A 11/1980 Price
4,321,659 A * 3/1982 Wheeler ..................... 362/293
4,516,190 A * 5/1985 Kloots ........................ 362/570
4,616,257 A 10/1986 Kloots
5,099,399 A * 3/1992 Miller et al. ................ 362/580
5,355,285 A 10/1994 Hicks
5,430,620 A 7/1995 Li
5,440,462 A * 8/1995 Kim et al. ................... 362/105
5,667,291 A 9/1997 Caplan
5,709,459 A 1/1998 Gourgouliatos
5,769,523 A 6/1998 Feinbloom
5,774,271 A * 6/1998 Lagerway et al. ........... 359/649
6,908,208 B1 * 6/2005 Hyde et al. ................. 362/105
RE39,162 E 7/2006 Caplan
7,134,763 B2 11/2006 Klootz
7,144,140 B2 * 12/2006 Sun et al. .................... 362/373
7,270,459 B2 * 9/2007 Waring ....................... 362/576
7,314,294 B1 * 1/2008 Moore ........................ 362/373
7,314,300 B1 * 1/2008 Dorr et al. .................. 362/581
2006/0285316 A1 * 12/2006 Tufenkjian et al. .......... 362/105

* cited by examiner

*Primary Examiner*—Hargobind S Sawhney
*Assistant Examiner*—David J Makiya
(74) *Attorney, Agent, or Firm*—Hiscock & Barclay, LLP

(57) ABSTRACT

Disclosed in this specification is a luminaire with a vented iris controller disposed on the external surface of the housing of the luminaire. The controller is for dilating and constricting the iris, thus controlling the size of the illuminated spot, wherein the iris controller is comprised of a hollow cylinder, rotatable relative to the housing. The cylinder has an inner ring and an outer ring, wherein the inner ring and outer ring are connected by a plurality of braces and vented spaces are present between each of the braces. Advantageously, the vented spaces help keep the outer ring cool, thus facilitating the operation of the iris controller by a user.

17 Claims, 10 Drawing Sheets

VENTED IRIS CONTROL FOR LUMINAIRE

FIELD OF THEE INVENTION

This invention relates, in one embodiment, to a iris control for a luminaire. The iris control is comprised of an inner ring and an outer ringer with vented spaces between such rings. The vented spaces promote cooling of the iris control.

BACKGROUND OF THE INVENTION

Head-mounted lights are widely used in many fields, including surgery and dentistry. Such a headlight, also known as an luminaire, is used to illuminate the surgical work area, but leaves the hands of the surgeon free to perform the surgery. Examples of surgical luminaire include U.S. Pat. No. 4,104,709 to Kloots (Surgeons Headlight with Continuously Variable Spot Size); U.S. Pat. No. 4,234,910 to Price (Head-Supported Illumination Device); U.S. Pat. No. 4,616,257 to Kloots et al. (Headlight); U.S. Pat. No. 5,355,285 to Hicks (Surgeon's Headlight System); U.S. Pat. No. 5,430,620 to Li et al. (Compact Surgical Illumination System Capable of Dynamically Adjusting the Resulting Field of Illumination); U.S. Pat. No. 5,667,291 and RE39,162 to Caplan et al. (Illumination Assembly for Dental and Medical Applications); U.S. Pat. No. 5,709,459 to Gourgouliatos et al. (Surgical Luminaire); U.S. Pat. No. 5,769,523 to Feinbloom (Surgical Headlamp with Dual Aperture Control); U.S. Pat. No. 6,908, 208 to Hyde et al. (Light to be Worn on Head); and U.S. Pat. No. 7,134,763 to Klootz (Illumination for Coaxial Variable Spot Headlight). While the medical industry has greatly benefited from the introduction of such headlamps, current lighting systems suffer from a number of deficiencies.

One such deficiency is the heat generated within the luminaire. Since the luminaire is disposed near the surgeon's forehead, the heat generated by the lamp is a cause for concern. Moreover, many luminaire contain an iris that permits the surgeon to adjust the size of the illuminated spot by controlling the degree of dilation or constriction of the iris. The degree of dilation or constriction of the iris is controlled by an iris controller which is mounted on the external surface of the luminaire housing. Unfortunately this controller, which must often be touched by the surgeon to control the iris, is often extremely hot—so much so that the beat may cause the surgeon to experience discomfort during adjustment of the iris. While several solutions to this problem have been attempted in the prior art, none has proven entirely satisfactory.

One complicating factor that must be considered when addressing this problem is the desirability of producing a small, lightweight luminaire. Since medical luminaire are typically attached to a surgeon's head, the size of the device is preferably small, such that the vision of the surgeon is not negatively impacted. Additionally, the luminaire must be lightweight, such that the surgeon will not find the weight of the device distracting. A compact luminaire with a cooled iris controller is desired.

SUMMARY OF THE INVENTION

The invention comprises, in one form thereof, a luminaire with a vented iris controller disposed on the external surface of the housing of the luminaire. The controller is for dilating and constricting the iris, wherein the iris controller is comprised of a hollow cylinder, rotatable relative to the housing. The cylinder has an inner ring and an outer ring, wherein the inner ring and outer ring are connected by a plurality of braces and vented spaces are present between each of the braces.

An advantage of the present invention is that the vented spaces keep the outer ring cool, which facilitates operation of the iris control by a user.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION OF A PREFERRED EMBODIMENT

Figure 1:
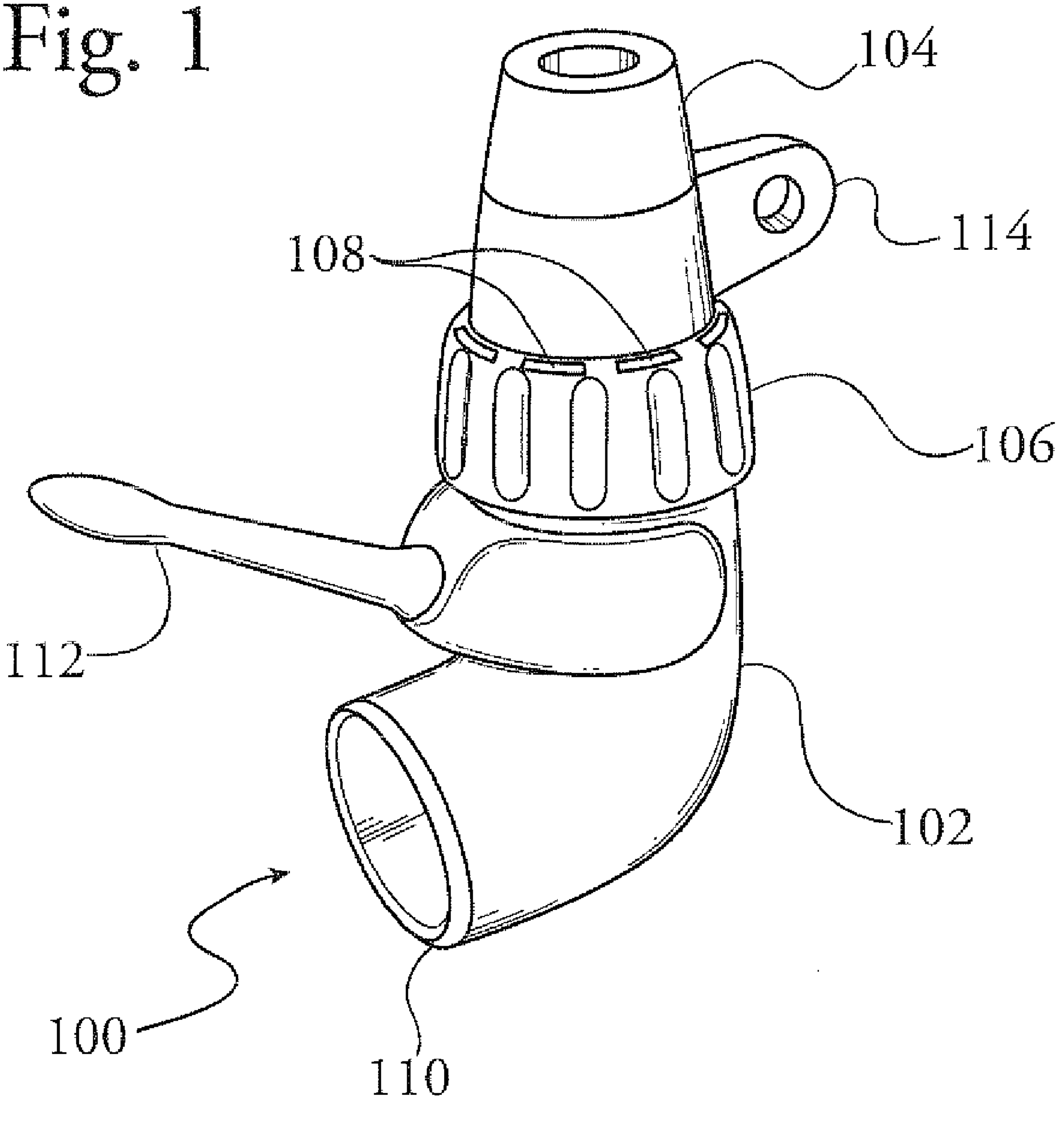
FIG. 1 is a perspective view of one illuminaire of the present invention.

Referring to FIG. 17 luminaire 100 is depicted. Luminaire 100 is comprised of housing 102 which has a receptacle end 104 and an aperture end 110. Receptacle end 104 may be configured to receive a cable, such as an electrical cable for powering a light source (not shown) disposed within the housing 102. In another embodiment, Receptacle end 104 is configured to receive a fiber optic cable that channels light from a remote source (not shown) to the luminaire 100. Aperture end 110 is configured to emit light from the luminaire 100 to a work surface, such as a surgical work area. Housing 102 is also equipped with handle 112 and connector 114. Connector 114 is on the external surface of the housing 102 and permits the luminaire 100 to be connected to a headband, as is customary in the art. In the embodiment depicted, connector 112 is a connector ring. In another embodiment, the connector is a ball and socket connector. Other suitable connectors are known in the art. Handle 112 permits the user to adjust the direction of illumination, relative to the headband, without touching the hot housing 102. Examples of such handles may be found in the prior art mentioned elsewhere in this specification.

Referring again to FIG. 1, housing 102 is also comprised of iris controller 106 which is rotatable relative to housing 102. Rotation of controller 106 controls the degree of dilation or constriction of the iris 200 (not shown in FIG. 1, but see FIG. 2) that is disposed within the housing 102. Controller 106 is comprised of vented spaces 108, which will be described in further detail elsewhere in this specification. As shown in FIG. 1, controller 106 is disposed on the external surface of housing 102 and between the receptacle end 104 and the aperture end 110.

Figure 2:
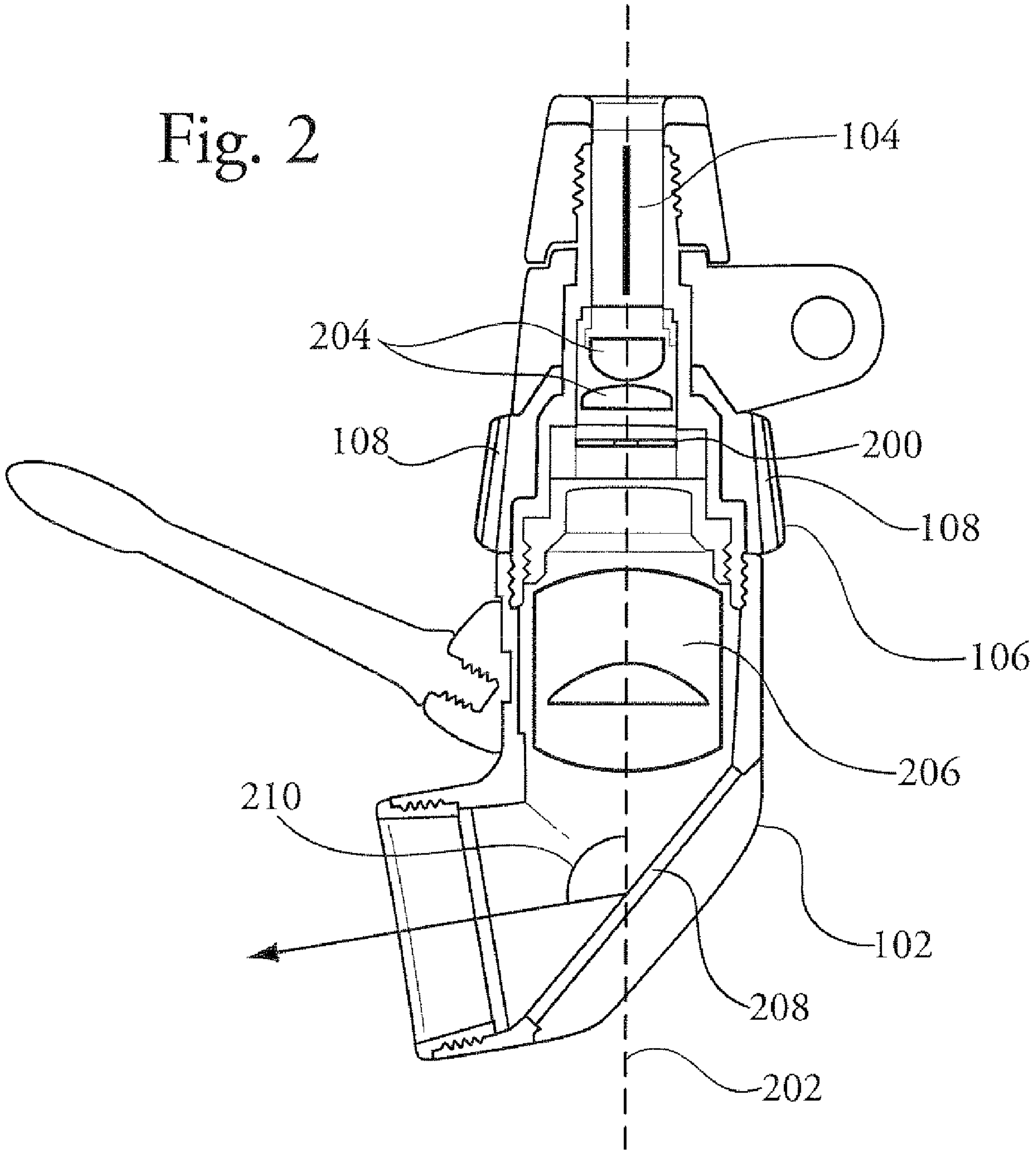
FIG. 2 is a schematic view of the illuminaire of FIG. 1 showing certain internal components of such illuminaire.

FIG. 2 is a schematic depiction of housing 102 of FIG. 1 which shows the internal components of luminaire 100. The main body of housing 102 is substantially cylindrical with a longitudinal axis 202. In the embodiment depicted in FIG. 2, receptacle end 104 is configured to receive a fiber optic cable that introduces light into housing 102. The light travels to a first lens system 204 and thereafter passes though iris 200, which is controlled by iris controller 106. Iris 200 is disposed within housing 102 and is between receptacle 104 and aperture end 110. The vented spaces 108 of iris controller 106 are visible in FIG. 2. After passing through iris 200, the light then enters a second lens system 206 before striking mirror 208. Mirror 208 reflects the light at an angle such that the light will pass through aperture end 110. In the embodiment depicted, aperture end 110 is at an angle 210 relative to the longitudinal axis 202. In the embodiment depicted, angle 210 is lightly greater than ninety degrees. When angle 210 is between about ninety and about one hundred ten degrees the vented spaces 108 have a substantially vertical configuration. As will be discussed in greater detail elsewhere in this specification, such a vertical configuration helps promote heat dissipation. In other embodiments, the angle 210 may be from about ninety degrees to about one hundred ten degrees. In yet another embodiment, the angle 210 is approximately one hundred eighty degrees (substantially straight) and no mirror is necessary. See, for example, U.S. Pat. No. 5,430,620 to Li et al. The aforementioned lens systems 204 and 206 are, in some embodiments, optional. Lens systems 204 and 206 may be conventional lens systems which are known in the art. For example, suitable condenser lens systems are disclosed in U.S. Pat. No. 4,104,709 to Kloots (Surgeons Headlight with Continuously Variable Spot Size. The iris controller 106 is depicted in greater detail in FIG. 3 and FIG. 4.

Figure 3:
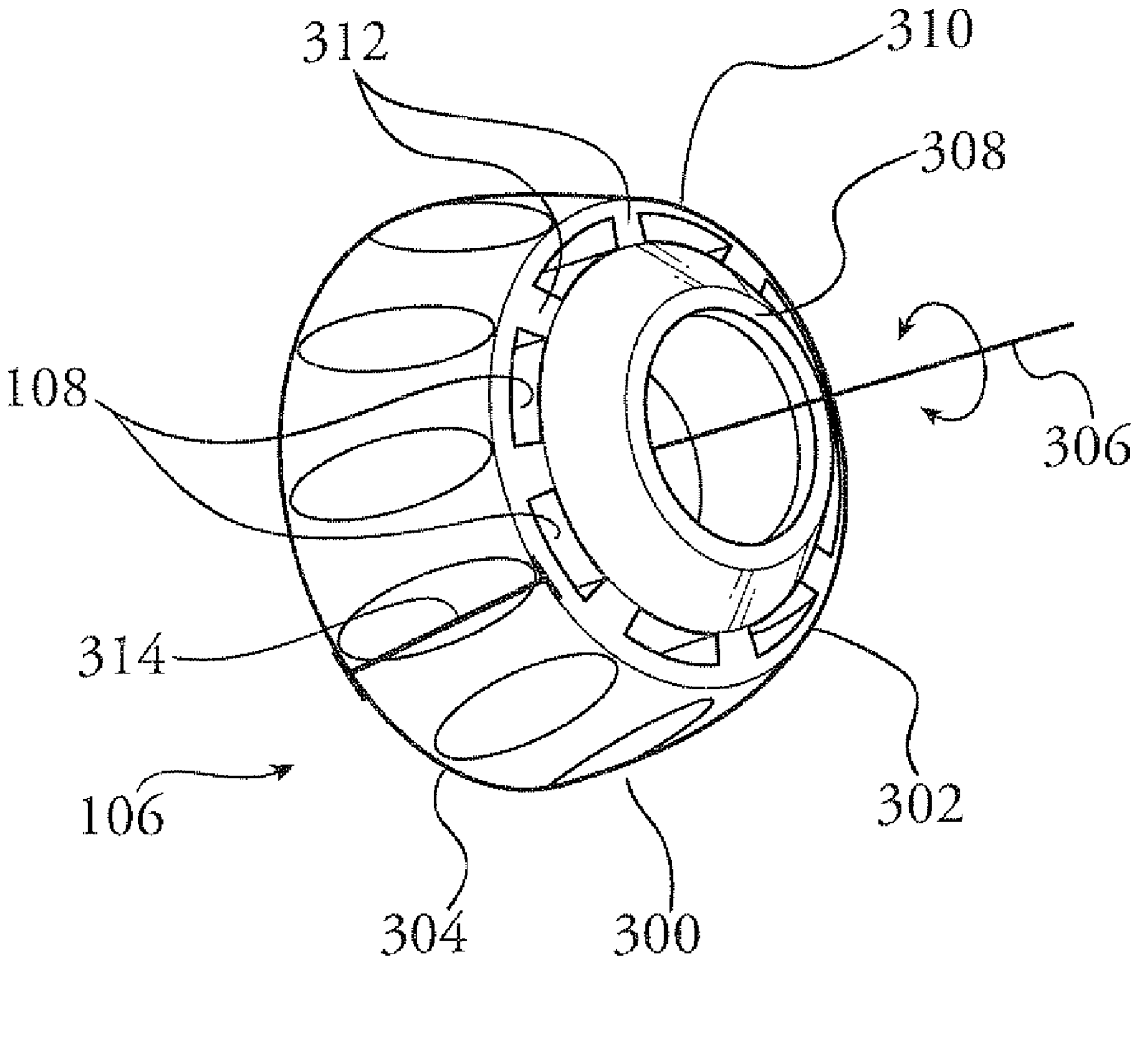
FIG. 3 is a perspective view of one iris controller of the invention.

FIG. 3 is a more detailed depiction of iris controller 106, wherein the housing 102 and iris 200 have been removed for the sake of clarity. Iris controller 106 is comprised of hollow cylinder 300 which has a top end 302 and a bottom end 304. As previously described, when controller 106 is disposed about housing 102, the controller is rotatable about axis of rotation 306. Such rotation controls the degree of dilation and constriction of the iris 200 (see FIG. 2). Hollow cylinder 300 is further comprised of an inner ring 308 and an outer ring 310. The inner ring 308 and outer ring 310 are connected to one another by a plurality of braces 312. Vented spaces 108 are present between each of the braces 312 and are disposed between the inner ring 308 and the outer ring 310 such that the volume of the vented spaces 108 is enclosed by such rings. The vented spaces 108 traverse the length 314 of hollow cylinder 300 such that the vented spaces open at both the top end 302 and the bottom end 304. The novel configuration of controller 106 includes certain advantageous structural features which are identified in FIG. 4.

Figure 4:
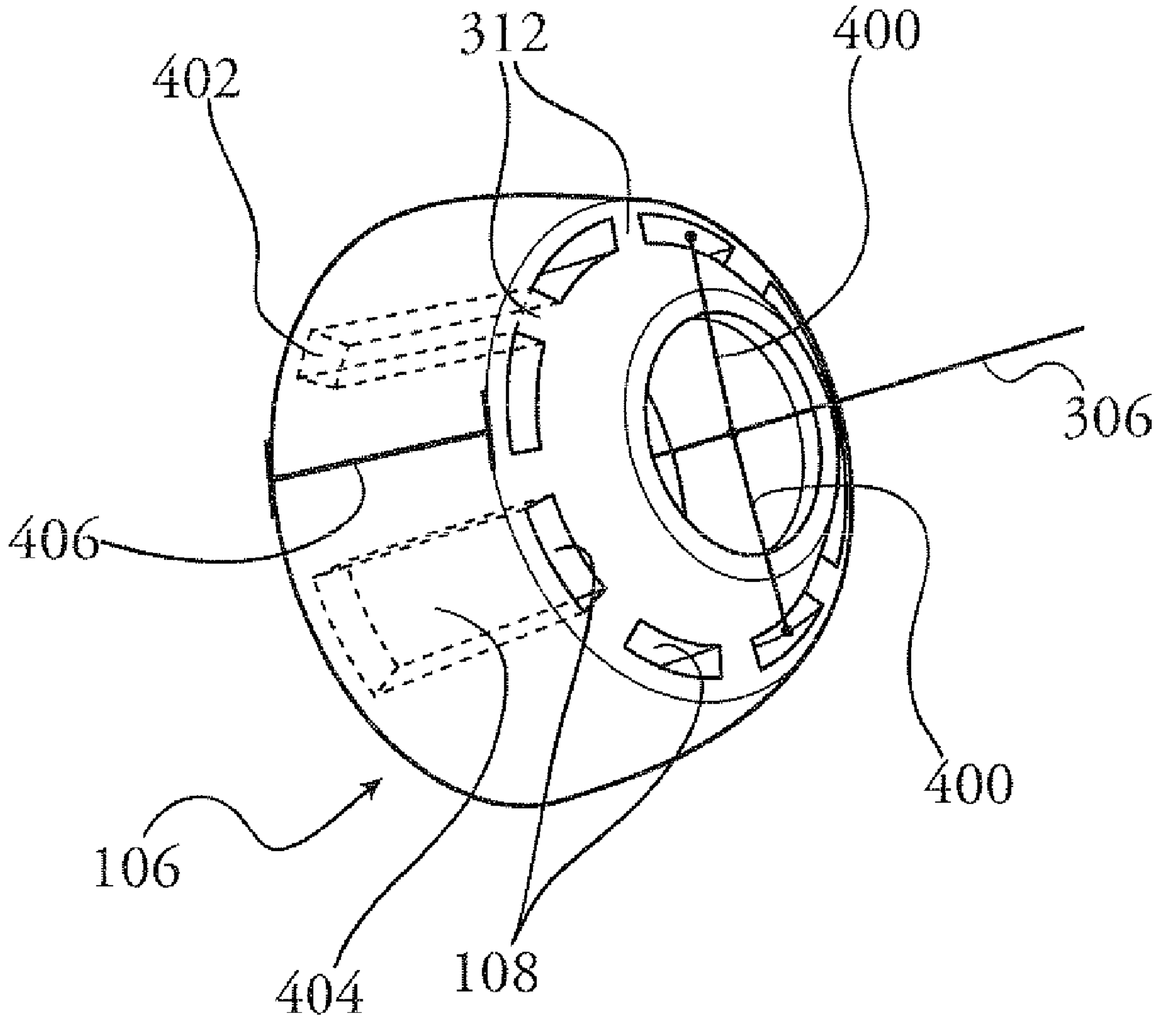
FIG. 4 is another depiction of the iris controller of FIG. 3.

FIG. 4 highlights certain features of iris controller 106 not explicitly shown in FIG. 3. As shown in FIG. 4, each of the vented spaces 108 is the same distance 400 from the axis of rotation 306. Advantageously, such a configuration helps to evenly dissipate heat from iris 200 (see FIG. 2). FIG. 4 also depicts the volume 402 of one brace and the volume 404 of one vented space. The volume is determined in a conventional manner—the volume is simply the product of the length 406, the width, and the height of the feature under consideration. Although only one such volume is shown in FIG. 4 for a brace and vented space, the volume of the other braces and vented spaces may be found in an analogous manner. Once the volume of the individual components has been determined, the sum of the volume of the vented spaces and the sum of the volume of the braces is then determined. Such volumes, or more specifically the sum of the exposed surfaces area of the inner ring 308, permit enhanced cooling of the iris controller 106 and provide insulation between inner ring 308 and outer ring 310.

As shown in FIG. 4, the volume 404 of the vented spaces is large compared to the volume 402 of the braces. Such a large volume 404 exposes the surface area of inner ring 308 to the air, and thus facilitates its cooling. Outer ring 310 provides a cooler surface where the user can grip the controller 106. Braces 312 serve to connect the inner ring 308 and outer ring 310 such that moving the outer ring 310 also moves the inner ring 308. It is desirable to expose the surface area of inner ring 308 (i.e. maximize the volume 404 of the vented spaces) while maintaining adequate structural support to of outer ring 310. Any suitable number of braces may thus be used. In the embodiment depicted, the sum of the volume of the vented spaces is greater than the sum of the volume of the braces, such that more than fifty percent of the surface area of the inner ring is exposed to the atmosphere. The remaining "surface" area of the inner ring is occupied by braces 312. In another embodiment, the sum of the volume of the vented spaces is at least twice the sum of the volume of the braces. In another embodiment, at least about seventy-five percent of the surface area of the inner ring is exposed to the atmosphere. When determining such a surface area, only the surface of the inner ring that faces the outer ring is measured. The surface of the inner ring that faces the iris is not measured. In one embodiment, shown in FIG. 4, the inner ring 308, outer ring 310, and braces 312 are unitary. Such a unitary configuration promotes the even dissipation of heat between such components and the environment.

As heat is transferred from the inner ring 308 to the air, the hot air rises and is carried away from iris controller 106. Advantageously, the axis of rotation 306 is substantially coaxial with respect to the longitudinal axis 202 of housing 102 (see FIG. 2) and the vented spaces 108 extend parallel to the axis of rotation 306. In certain embodiments, the longitudinal axis is held substantially perpendicular to the surface of the earth during use of the light, thus the vented spaces 108 are vertically disposed. Due to this substantially vertical configuration, the hot air is easily carried away from iris controller 106 by simple convection. While a substantially vertical configuration is desirable, deviation from a purely vertical configuration will still result in adequate convection.

Figure 5:
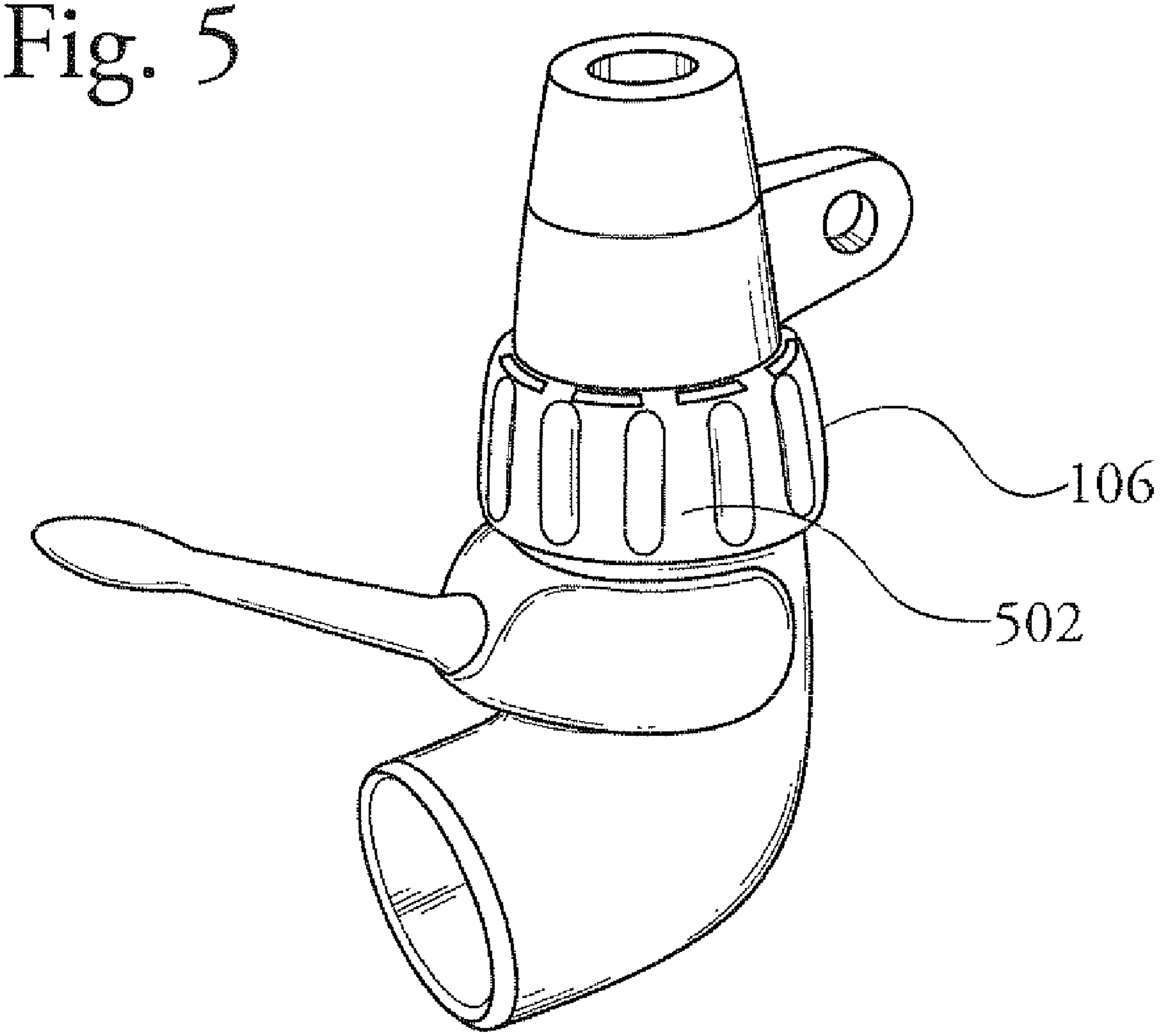
FIG. 5 is a perspective view of the illuminaire of FIG. 1 which illustrates points where temperature measures were obtained.

The advantageous features described above were subjected to testing by obtaining temperature measurements along the external surface of the iris controller 106. The temperature was taken at point 500, as shown in FIG. 5. The controller 106 was adjusted such that the opening of iris 200 was set at a certain diameter. Thereafter, light was passed through the device and the temperature was recorded every fifteen minutes. One test was conducted wherein vented spaces 108 were present as described above. Another test was conducted wherein no vented spaces were present (i.e. a control). The test results are depicted in FIGS. 6-10.

Figure 6:
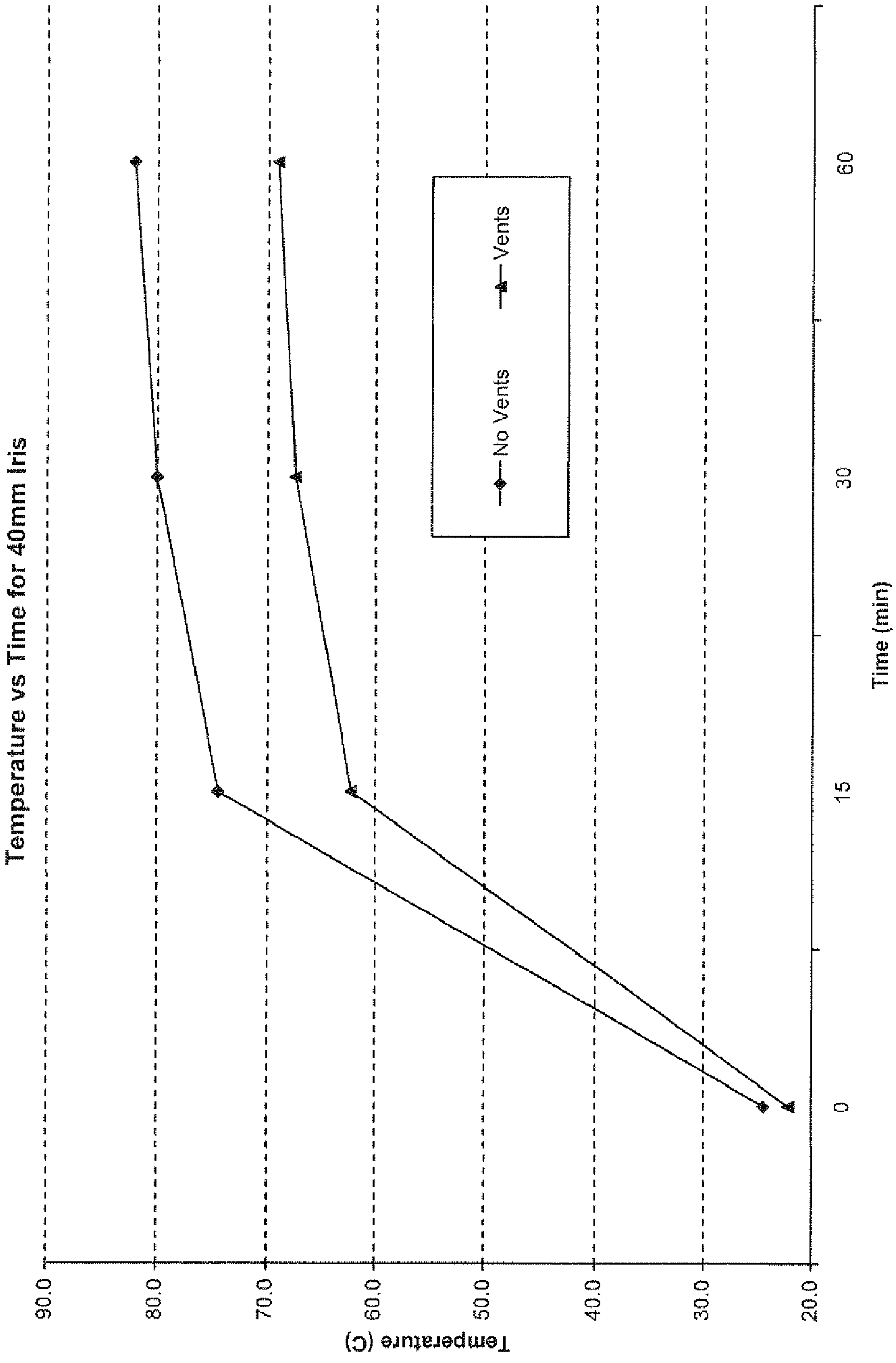
FIG. 6 to FIG. 10 are graphs of the temperature of the iris controller versus the time elapsed since the light was activated for certain iris dilation values.

Referring to FIG. 6, the iris was adjusted such that the opening of the iris measured forty millimeters across. Temperature measurements were taken every fifteen minutes. The resulting data is depicted below and in FIG. 6.

| Time (min) | No Vents - | Vents - |
|---|---|---|
| 0 | 24.4° C. | 22.1° C. |
| 15 | 74.5° C. | 62.2° C. |
| 30 | 80.0° C. | 67.4° C. |
| 60 | 82.1° C. | 69.1° C. |

As shown, the temperature rapidly rose within the first fifteen minutes of activating the light. The non-vented control test achieved a temperature of approximately 82° C. (point 500) after sixty minutes. The vented embodiment achieved a temperature of approximately 69° C. (point 500). Inclusion of the vented spaces 108 thus afforded a temperature advantage of approximately 13° C.

Figure 7:
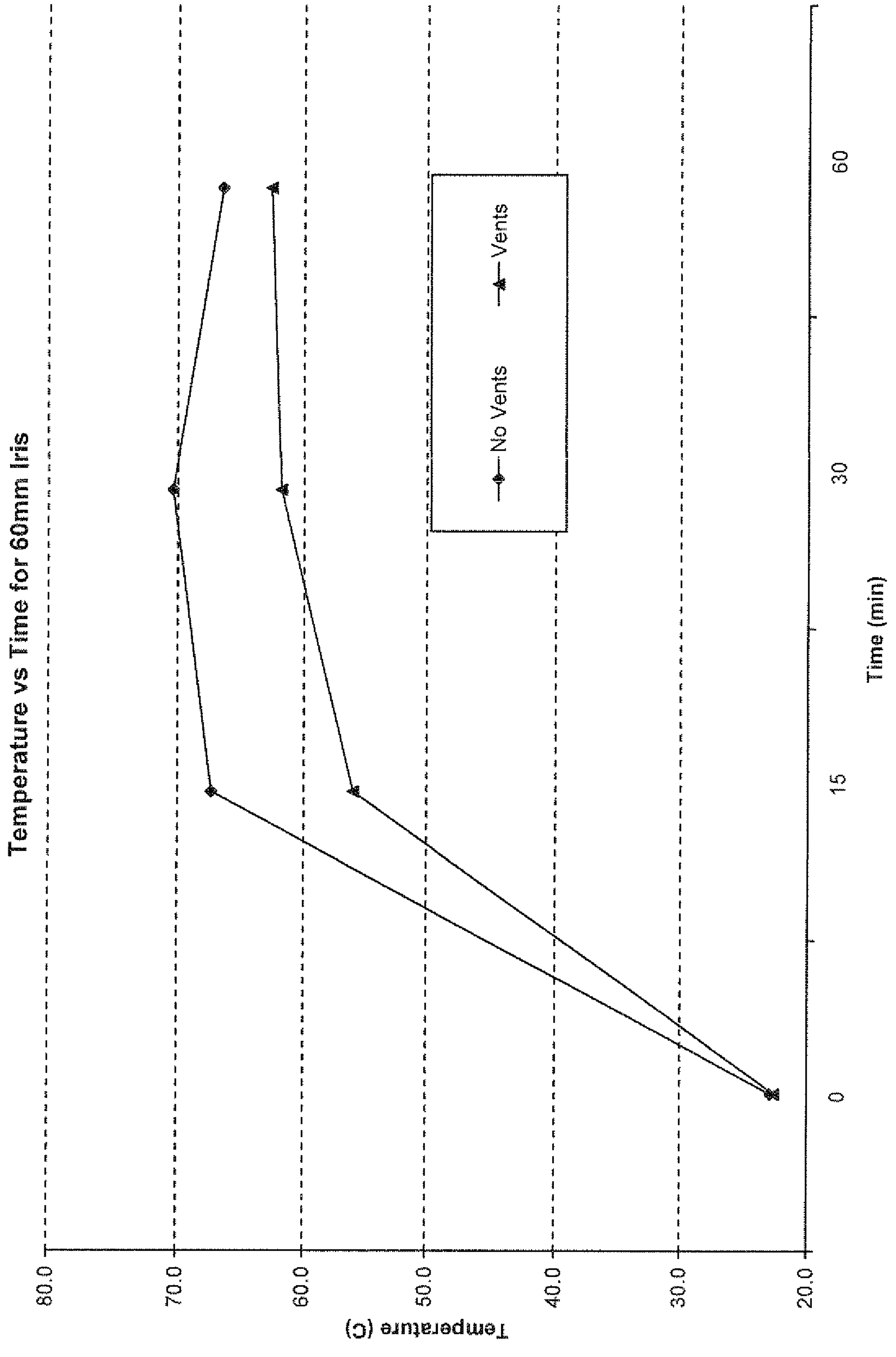

Referring to FIG. 7, the iris was adjusted such that the opening of the iris measured sixty millimeters across. Temperature measurements were taken every fifteen minutes. The resulting data is depicted below and in FIG. 7.

| Time (min) | No Vents - | Vents - |
|---|---|---|
| 0 | 22.8° C. | 22.5° C. |
| 15 | 67.2° C. | 55.9° C. |
| 30 | 70.2° C. | 61.7° C. |
| 60 | 66.3° C. | 62.5° C. |

As shown, the temperature rapidly rose within the first fifteen minutes of activating the light. The non-vented control test achieved a temperature of approximately 66° C. (point 500) after sixty minutes. The vented embodiment achieved a temperature of approximately 63° C. (point 500). Inclusion of the vented spaces 108 thus afforded a temperature advantage of approximately 5° C. It is noteworthy that the temperature of the iris controller 106 decreases as the iris 200 is dilated. As more light energy is allowed to pass through the housing 102, less of such light energy is converted into heat. As the iris 200 is further dilated, the temperature advantage provided by the vented spaces 108 continues to diminish (see FIGS. 8-10).

Figure 8:
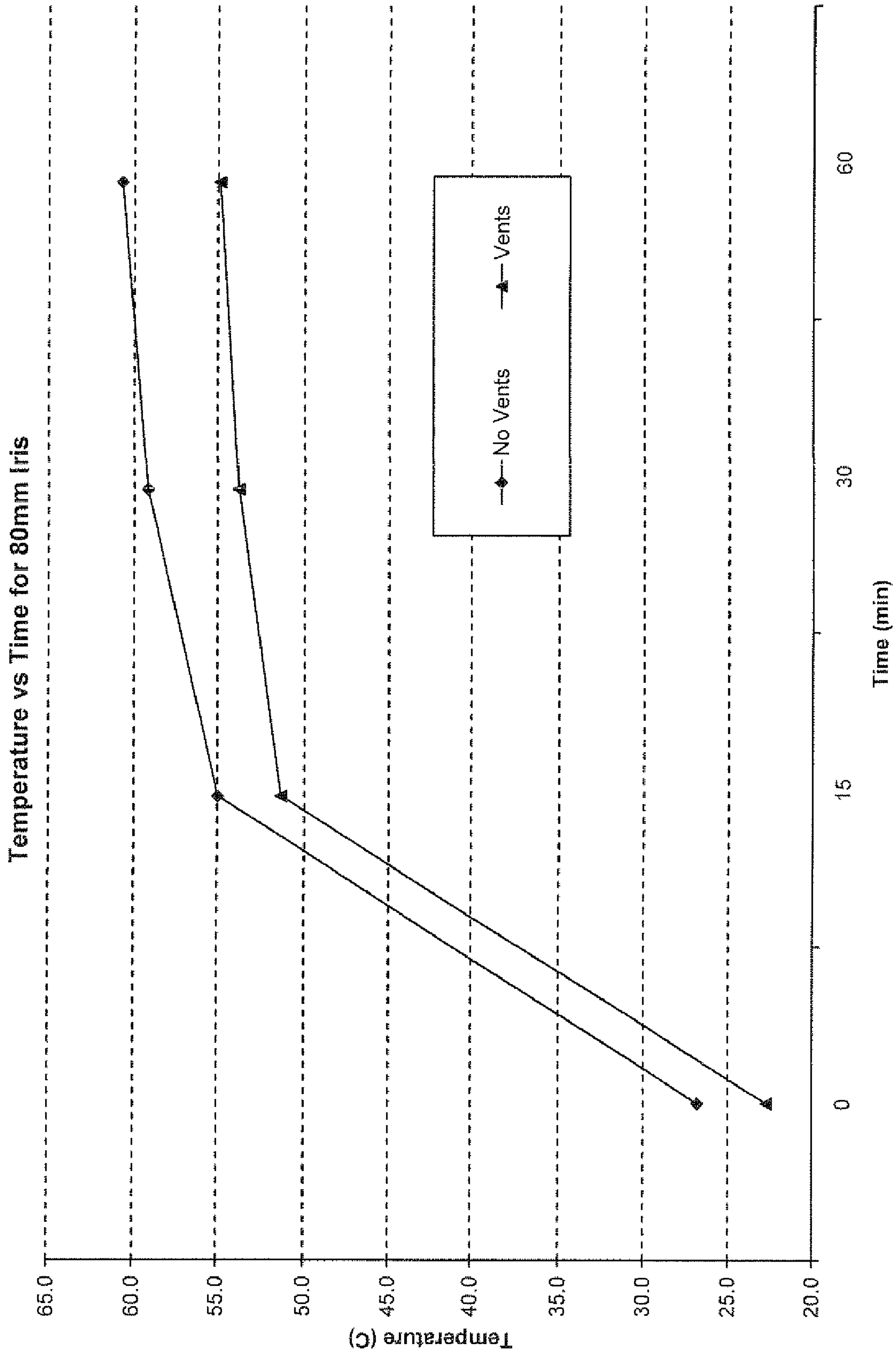

Referring to FIG. 8, the iris was adjusted such that the opening of the iris measured eighty millimeters across. Temperature measurements were taken every fifteen minutes. The resulting data is depicted below and in FIG. 8.

| Time (min) | No Vents - | Vents - |
|---|---|---|
| 0 | 26.7° C. | 22.6° C. |
| 15 | 55.0° C. | 51.3° C. |
| 30 | 59.1° C. | 53.8° C. |
| 60 | 60.6° C. | 54.9° C. |

As shown, the temperature rapidly rose within the first fifteen minutes of activating the light. The non-vented control test achieved a temperature of approximately 61° C. (point 500) after sixty minutes. The vented embodiment achieved a temperature of approximately 55° C. (point 500). Inclusion of the vented spaces 108 thus afforded a temperature advantage of approximately 5° C.

Figure 9:
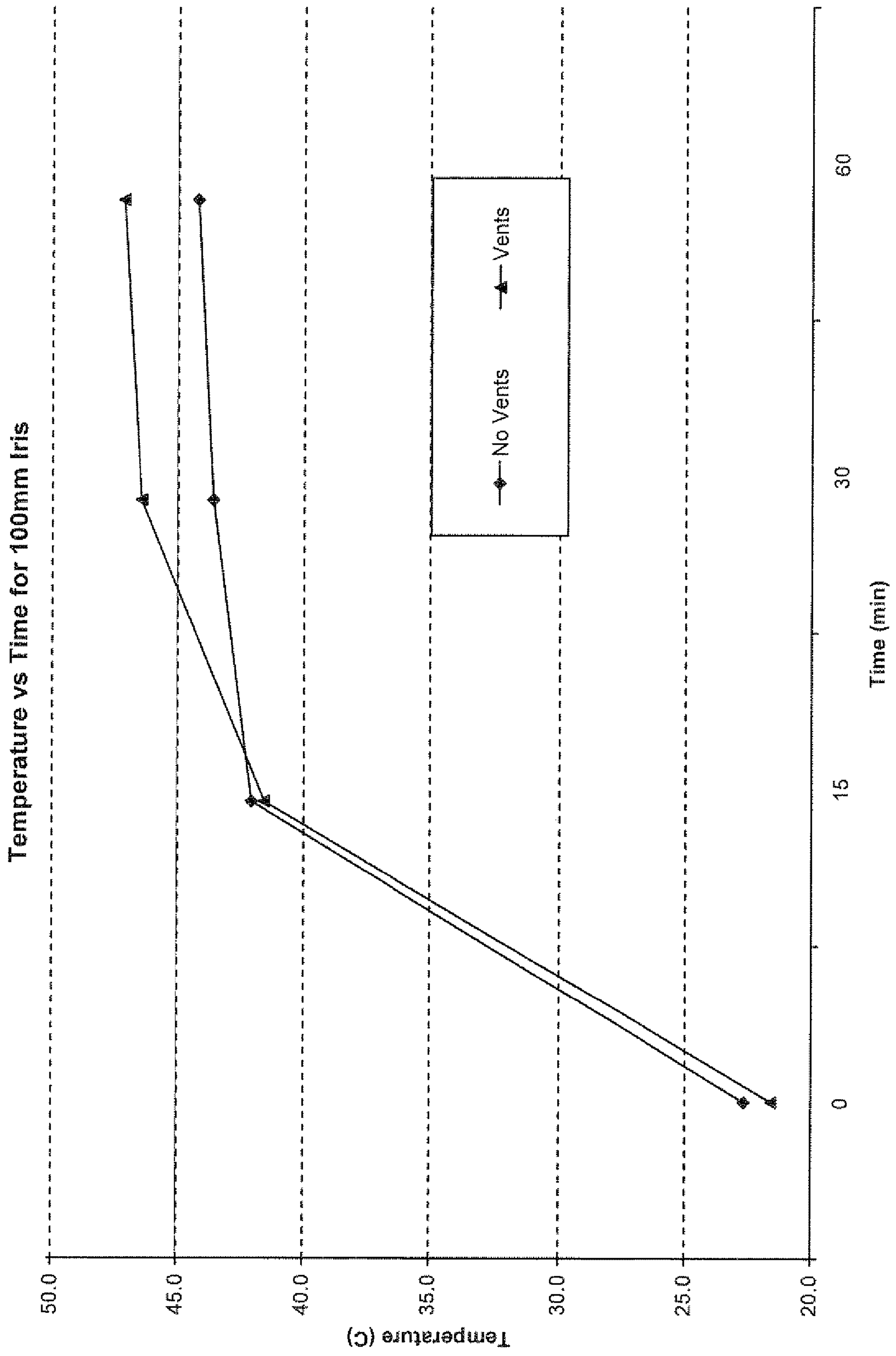

Referring to FIG. 9, the iris was adjusted such that the opening of the iris measured one hundred millimeters across. Temperature measurements were taken every fifteen minutes. The resulting data is depicted below and in FIG. 9.

| Time (min) | No Vents - | Vents - |
|---|---|---|
| 0 | 22.7° C. | 21.6° C. |
| 15 | 42.1° C. | 41.6° C. |
| 30 | 43.6° C. | 46.4° C. |
| 60 | 44.2° C. | 47.1° C. |

As shown, the temperature rapidly rose within the first fifteen minutes of activating the light. The non-vented control test achieved a temperature of approximately 44° C. (point 500) after sixty minutes. The vented embodiment achieved a temperature of approximately 47° C. (point 500). The temperature advantage provided by the vented spaces is modest when the iris is extremely dilated and the temperature of the iris controller 106 is relatively low.

Figure 10:
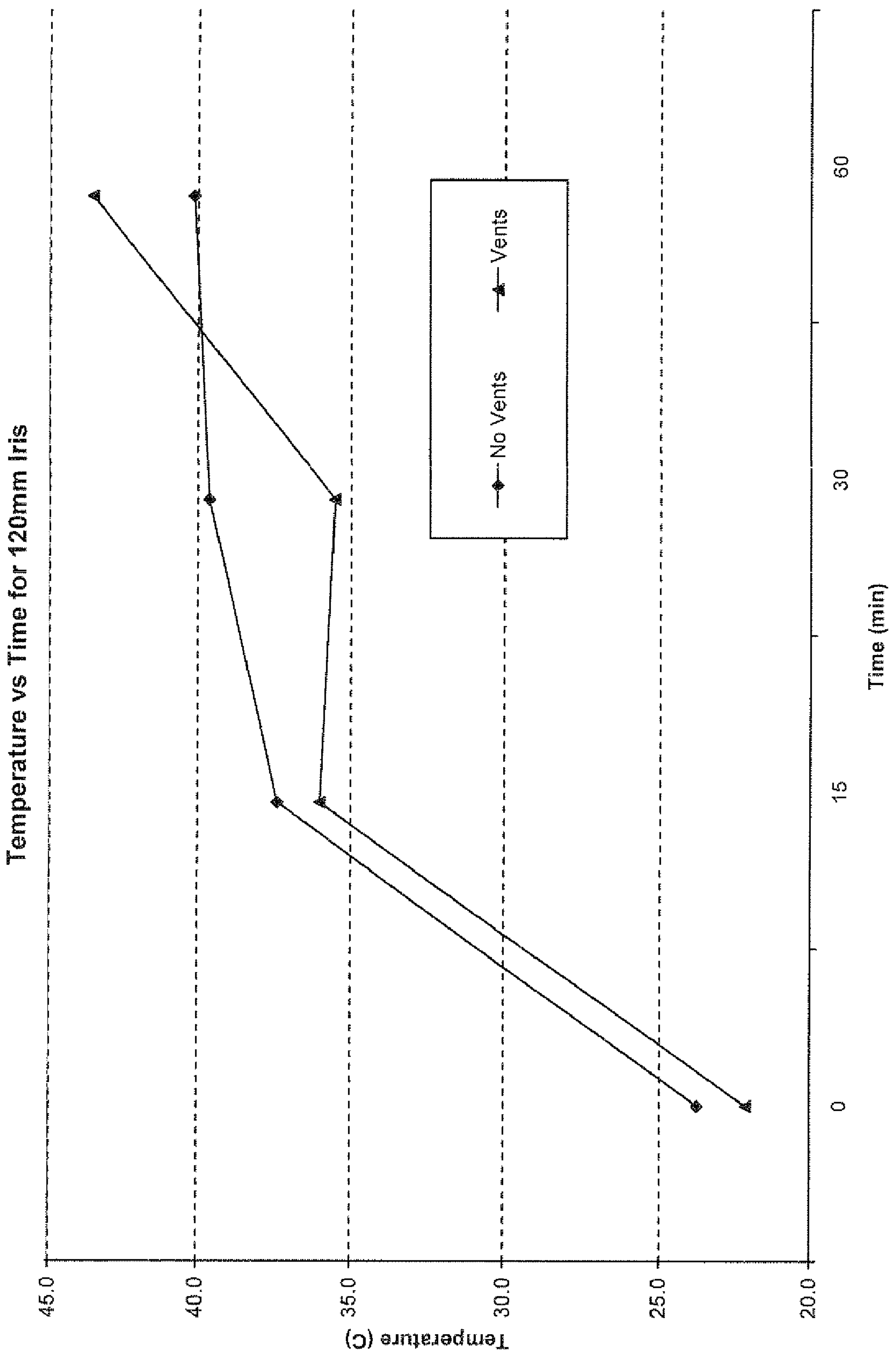

Referring to FIG. 10, the iris was adjusted such that the opening of the iris measured one hundred twenty millimeters across. Temperature measurements were taken every fifteen minutes. The resulting data is depicted below and in FIG. 10.

| Time (min) | No Vents - | Vents - |
|---|---|---|
| 0 | 23.7° C. | 22.1° C. |
| 15 | 37.5° C. | 36.1° C. |
| 30 | 39.7° C. | 35.6° C. |
| 60 | 40.2° C. | 43.5° C. |

As shown, the temperature rapidly rose within the first fifteen minutes of activating the light. The non-vented control test achieved a temperature of approximately 40° C. (point 500) after sixty minutes. The vented embodiment achieved a temperature of approximately 44° C. (point 500). Again, the temperature advantage provided by the vented spaces is modest when the iris is extremely dilated and the temperature of the iris controller 106 is relatively low.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A luminaire with a vented iris controller comprising a) a housing comprising a receptacle end for receiving a cable, an aperture end for emitting light, and an iris disposed within the housing and between the receptacle end and the aperture end, b) an iris controller operatively attached to the housing between the receptacle end and the aperture end for selectively dilating and constricting the iris, said iris controller including a hollow cylinder, rotatable relative to the housing about an axis of rotation, said cylinder having a top end, a bottom end, an inner ring entirely disposed internal to the housing, and an outer grippable ring, at least a portion of which is disposed external to the housing, wherein i the inner ring and outer ring of said controller are connected by a plurality of braces in which a vented space is present between each of said braces, ii each vented space traversing the length of the cylinder such that the vented spaces open at both the top end and the bottom end, said vented spaces being disposed external to the housing within said outer grippable ring wherein venting of heat built up within said housing to atmosphere occurs through said vented spaces without proximate structure at either end thereof preventing same.

2. The luminaire as recited in claim 1, wherein the sum of the volume of the vented spaces is greater than the sum of the volume of the braces.

3. The luminaire as recited in claim 1, wherein the sum of the volume of the vented spaces is at least twice the sum of the volume of the braces.

4. The luminaire as recited in claim 1, wherein the sum of the volume of the vented spaces is at least triple the sum of the volume of the braces.

5. The luminaire as recited in claim 1, wherein each of the vented spaces is the same distance from the axis of rotation.

6. The luminaire as recited in claim 1, wherein the housing has a longitudinal axis and the axis of rotation of the iris controller is substantially coaxial with respect to the longitudinal axis.

7. The luminaire as recited in claim 6, wherein the aperture end is disposed at an angle of from about 90 degrees to about 110 degrees, relative to the longitudinal axis, and the luminaire further comprises a mirror for reflecting light at the angle of from about 90 degrees to about 110 degrees out of the aperture end.

8. The luminaire as recited in claim 1, wherein the vented spaces extend parallel to the axis of rotation.

9. The luminaire as recited in claim 1, further comprising a connector on the external surface of the housing for connecting to a headband.

10. The luminaire as recited in claim 1, further comprising a handle.

11. The luminaire as recited in claim 1, wherein the inner ring, outer ring, and braces are unitary.

12. A luminaire with a vented iris controller comprising a) a housing comprising a receptacle end for receiving a cable, an aperture end for emitting light, and an iris disposed within the housing and between the receptacle end and the aperture end, b) an iris controller, disposed on an external surface of the housing between the receptacle end and the aperture end, for dilating and constricting the iris, wherein the iris controller is comprised of a hollow cylinder, rotatable relative to the housing, with a top end, a bottom end, an inner ring entirely disposed internal to the housing, an outer ring having at least a portion disposed external to the housing, and an axis of rotation, wherein i the iris being operatively connected to the inner ring, the inner ring being connected to the outer ring by a plurality of braces and vented spaces are present between each of the braces, wherein the inner ring, outer ring, and braces are unitary, ii the vented spaces traverse the length of the cylinder such that the vented spaces open at both the top end and the bottom end, said vented spaces disposed in the portion of said outer ring that is external to the housing and without proximate structure at either end of said spaces in order to permit venting of heat to atmosphere, iii the sum of the volume of the vented spaces is greater than the sum of the volume of the braces, c) wherein the housing has a longitudinal axis and the axis of rotation of the iris controller is substantially coaxial with respect to the longitudinal axis of the housing, d) wherein the aperture end is disposed at an angle of from about 90 degrees to about 110 degrees, relative to the longitudinal axis, and the luminaire further comprises a mirror for reflecting light at the angle of from about 90 degrees to about 110 degrees out of the aperture end.

13. The luminaire as recited in claim 12, wherein the sum of the volume of the vented spaces is at least twice the sum of the volume of the braces.

14. The luminaire as recited in claim 12, further comprising a connector on the external surface of the housing for connecting to a headband.

15. A luminaire with a vented iris controller comprising a) a housing comprising a receptacle end for receiving a fiber optic cable, an aperture end for emitting light from the fiber optic cable, and an iris disposed within the housing and between the receptacle end and the aperture end, b) an iris controller, disposed on an external surface of the housing between the receptacle end and the aperture end, for dilating and constricting the iris, wherein the iris controller is comprised of a hollow cylinder, rotatable relative to the housing, with a top end, a bottom end, an inner ring disposed internal to the housing, an outer ring having at least a portion disposed external to the housing, and an axis of rotation, wherein i the inner ring and outer ring are connected by a plurality of braces and vented spaces are present between each of the braces, wherein the inner ring, outer ring, and braces are unitary, ii each of the vented spaces traversing the length of the cylinder such that the vented spaces open at both the top end and the bottom end, said vented spaces being disposed in said portion of said outer ring that is external to the housing and without proximate structure at either end of said vented spaces to enable venting to atmosphere, iii the sum of the volume of the vented spaces is greater than the sum of the volume of the braces, iv the inner ring, the outer ring, and the plurality of braces are unitary, c) wherein the housing has a longitudinal axis and the axis of rotation of the iris controller is substantially coaxial with respect to the longitudinal axis of the housing, d) wherein the aperture end is disposed at an angle of from about 90 degrees to about 110 degrees, relative to the longitudinal axis, and the luminaire further comprises a mirror for reflecting light at the angle of from about 90 degrees to about 110 degrees out of the aperture end.

16. The luminaire as recited in claim 15, further comprising a first lens system disposed between the receptacle end and the iris.

17. The luminaire as recited in claim 16, further comprising a second lens system disposed between the iris and the aperture end.

* * * * *